(12) United States Patent
Foerster et al.

(10) Patent No.: US 6,547,800 B2
(45) Date of Patent: Apr. 15, 2003

(54) METHOD AND APPARATUS FOR ATTACHING CONNECTIVE TISSUES TO BONE USING A CORTICAL BONE ANCHORING DEVICE

(75) Inventors: Seth A. Foerster, San Clemente, CA (US); Norman S. Gordon, Irvine, CA (US)

(73) Assignee: Opus Medical, Inc., San Juan Capistrano, CA (US)

( * ) Notice: Subject to any disclaimer, the term of this patent is extended or adjusted under 35 U.S.C. 154(b) by 56 days.

(21) Appl. No.: 09/876,260

(22) Filed: Jun. 6, 2001

(65) Prior Publication Data

US 2002/0188305 A1 Dec. 12, 2002

(51) Int. Cl.$^7$ .......................... A61B 17/04; A61B 17/84
(52) U.S. Cl. ........................................ 606/151; 606/232
(58) Field of Search ................................ 606/151, 232, 606/72, 75; 411/34

(56) References Cited

U.S. PATENT DOCUMENTS

| | | | |
|---|---|---|---|
| 5,417,691 A | | 5/1995 | Hayhurst |
| 5,417,712 A | | 5/1995 | Whittaker et al. |
| 5,618,314 A | * | 4/1997 | Harwin et al. ................. 606/72 |
| 5,941,900 A | | 8/1999 | Bonutti |
| 6,045,574 A | | 4/2000 | Thal |
| 6,146,406 A | | 11/2000 | Shluzas et al. |
| 6,328,758 B1 | * | 12/2000 | Tornier et al. ............... 606/232 |

* cited by examiner

Primary Examiner—Peter Nerbun
(74) Attorney, Agent, or Firm—Stout, Uxa, Buyan & Mullins, LLP; Donald E. Stout

(57) ABSTRACT

A bone anchor device for attaching connective tissue to bone comprises a disk adapted for insertion into a portion of bone to which the connective tissue is to be attached. The disk is movable between a bent orientation for presenting a smaller cross-section and an expanded orientation for presenting a larger cross-section. The bent orientation is utilized for inserting the disk through a small hole into a region of cancellous bone beneath the cortical bone layer, after which the disk is actuated to its expanded orientation so that it will be permanently anchored in the cancellous bone, as it will be too large to return proximally through the hole in the cortical bone layer. Two embodiments are disclosed. In a first embodiment, the disk is initially formed in the expanded orientation, of spring steel. In a second embodiment, the disk is initially formed in the bent orientation, and spring steel is not required.

33 Claims, 13 Drawing Sheets

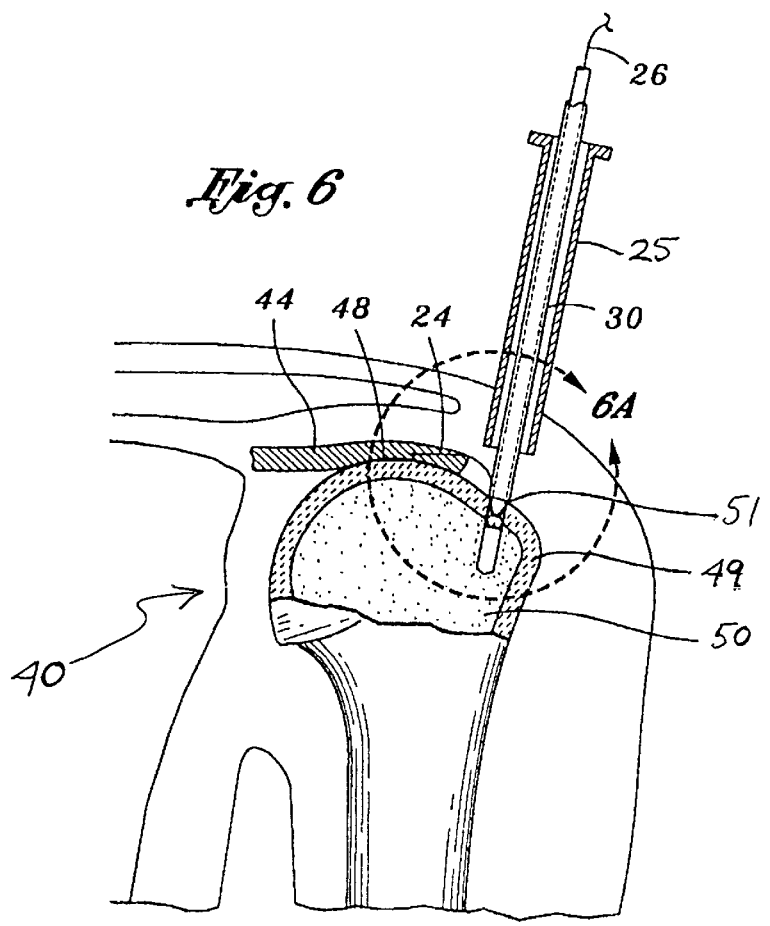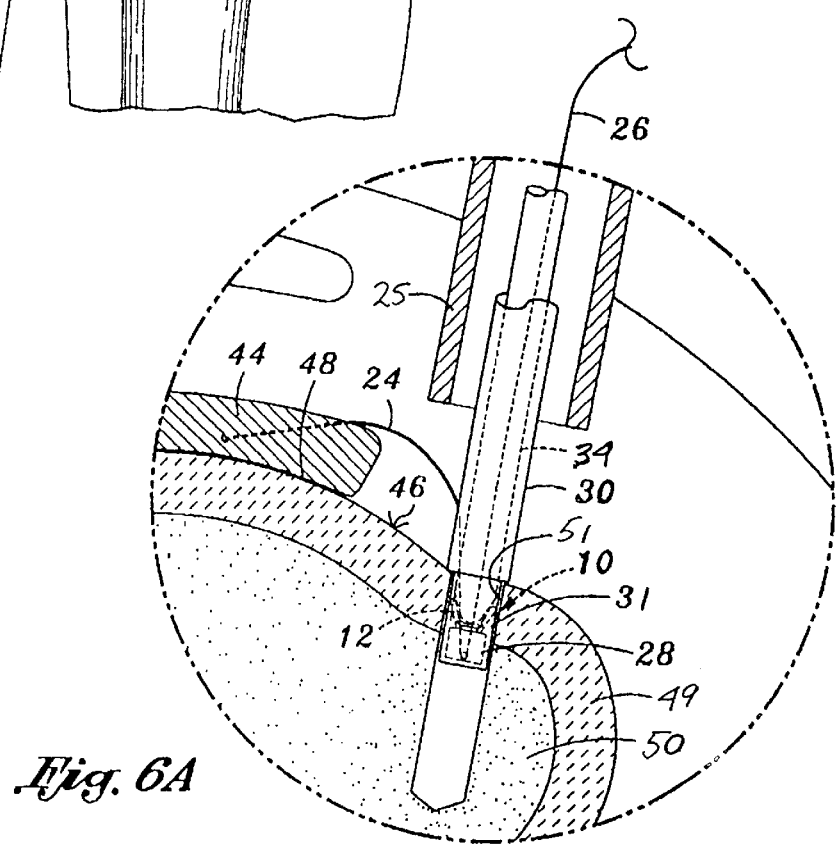

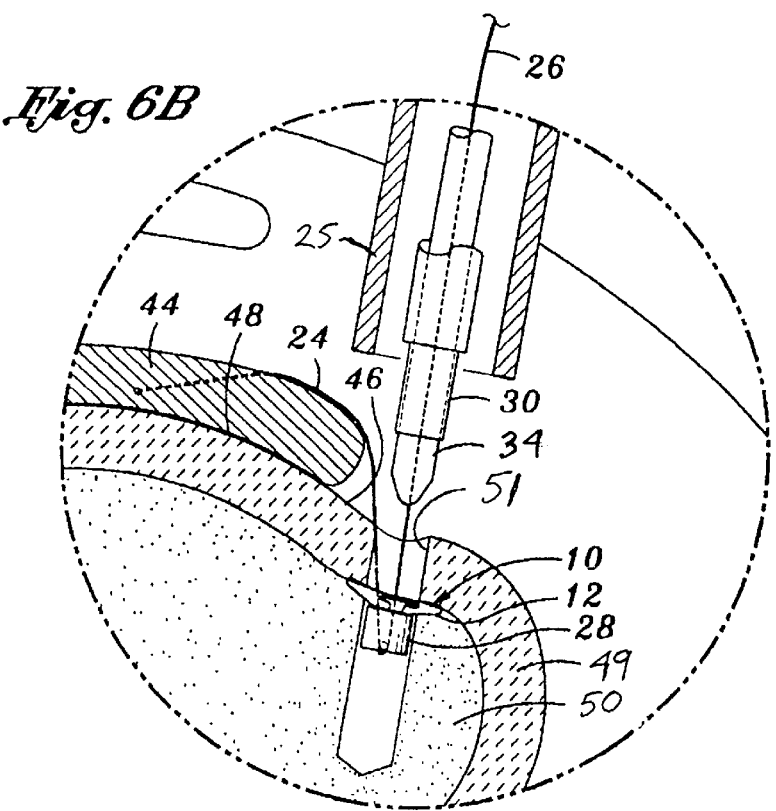
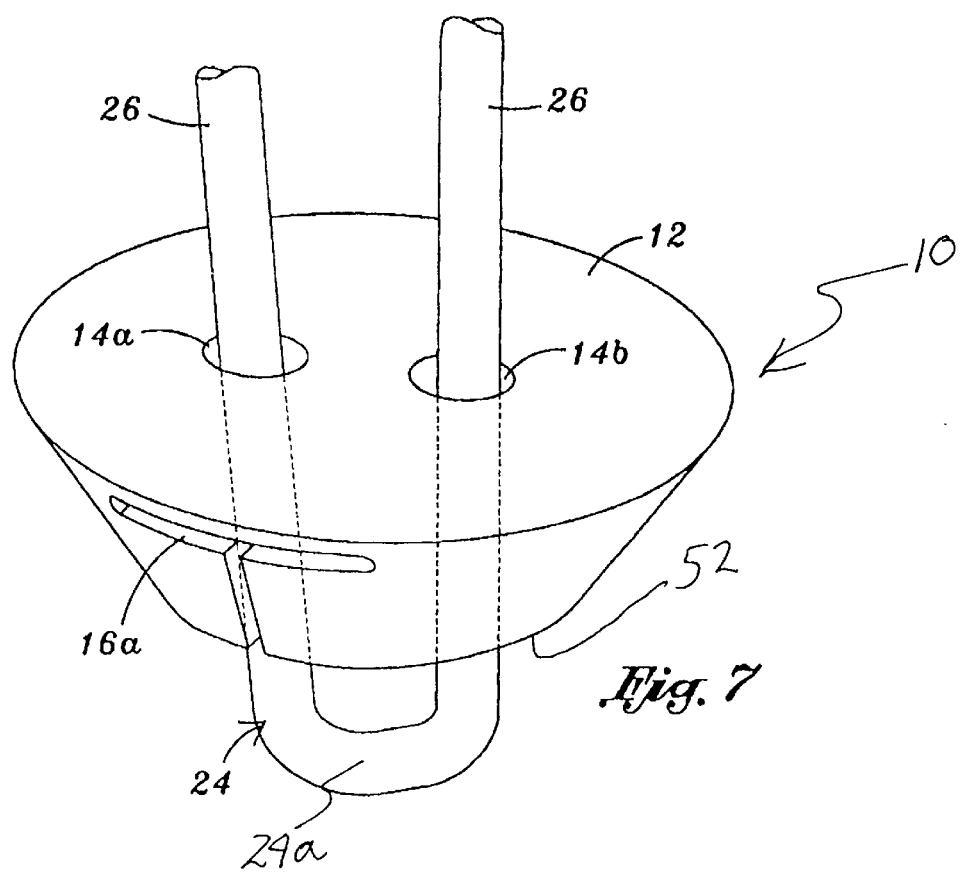

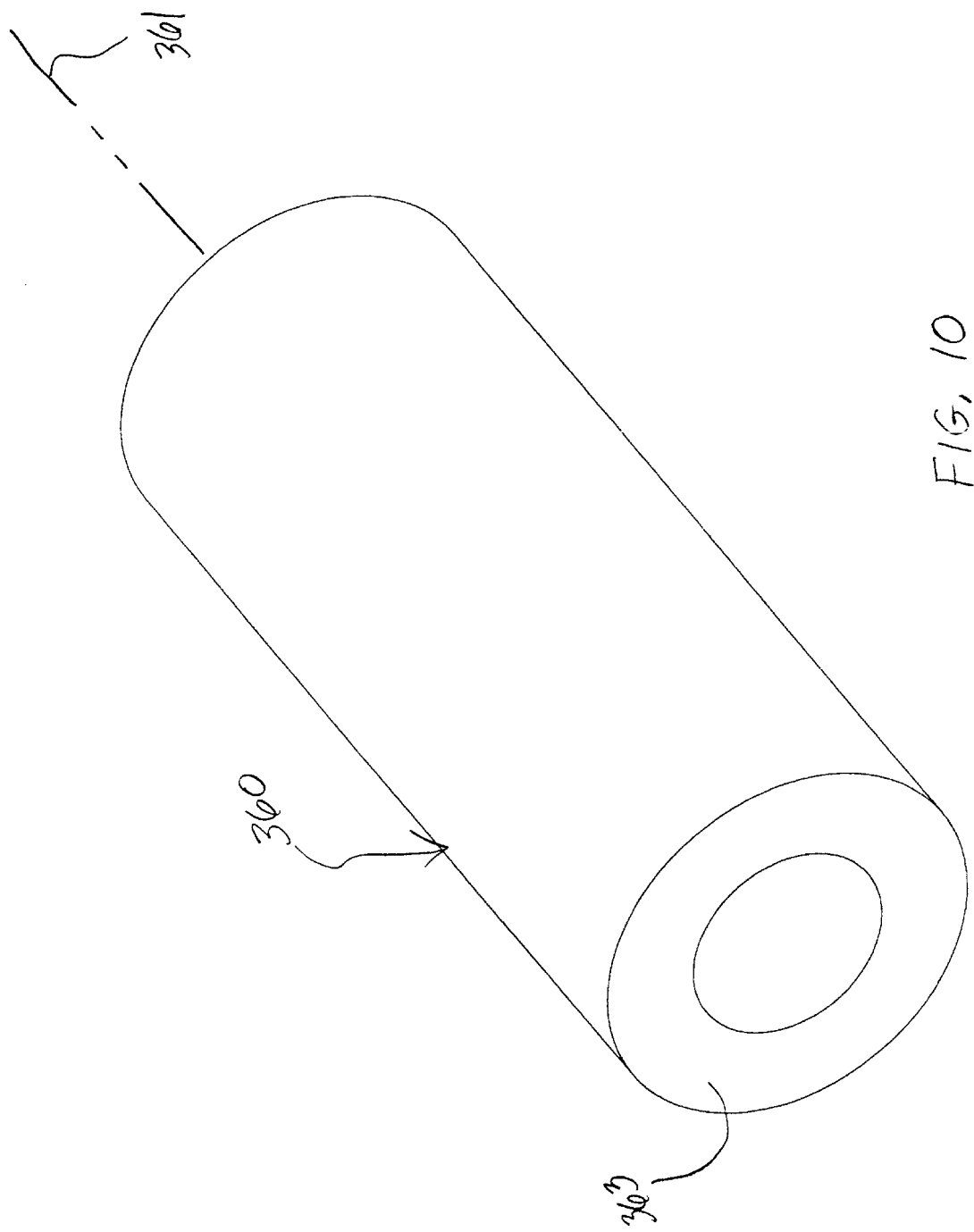

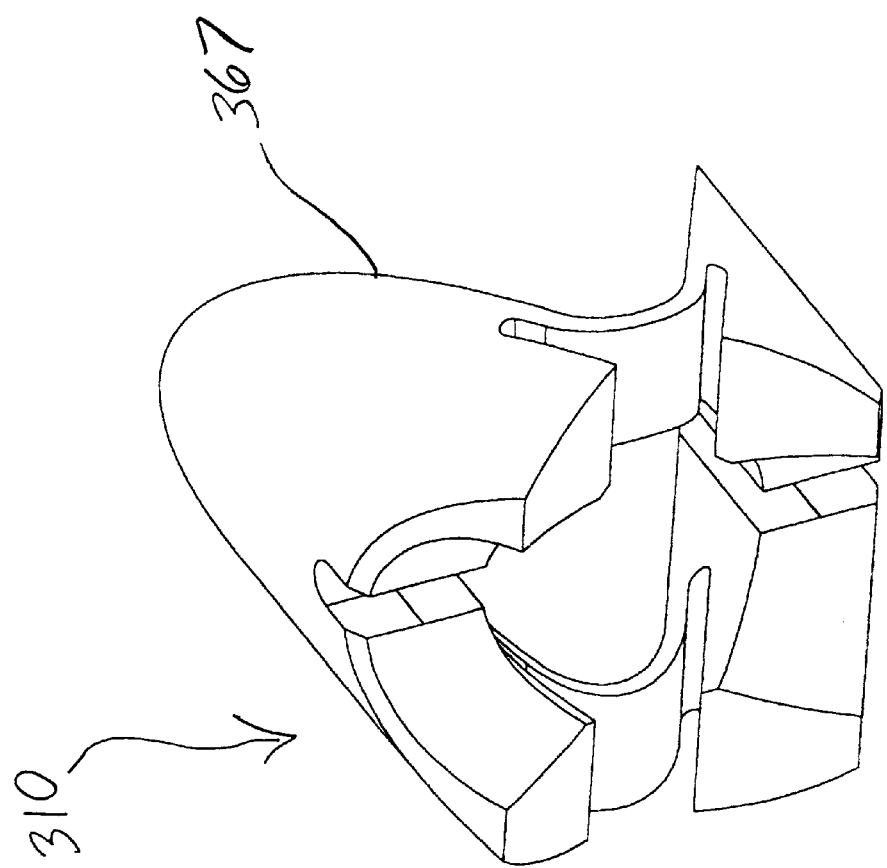

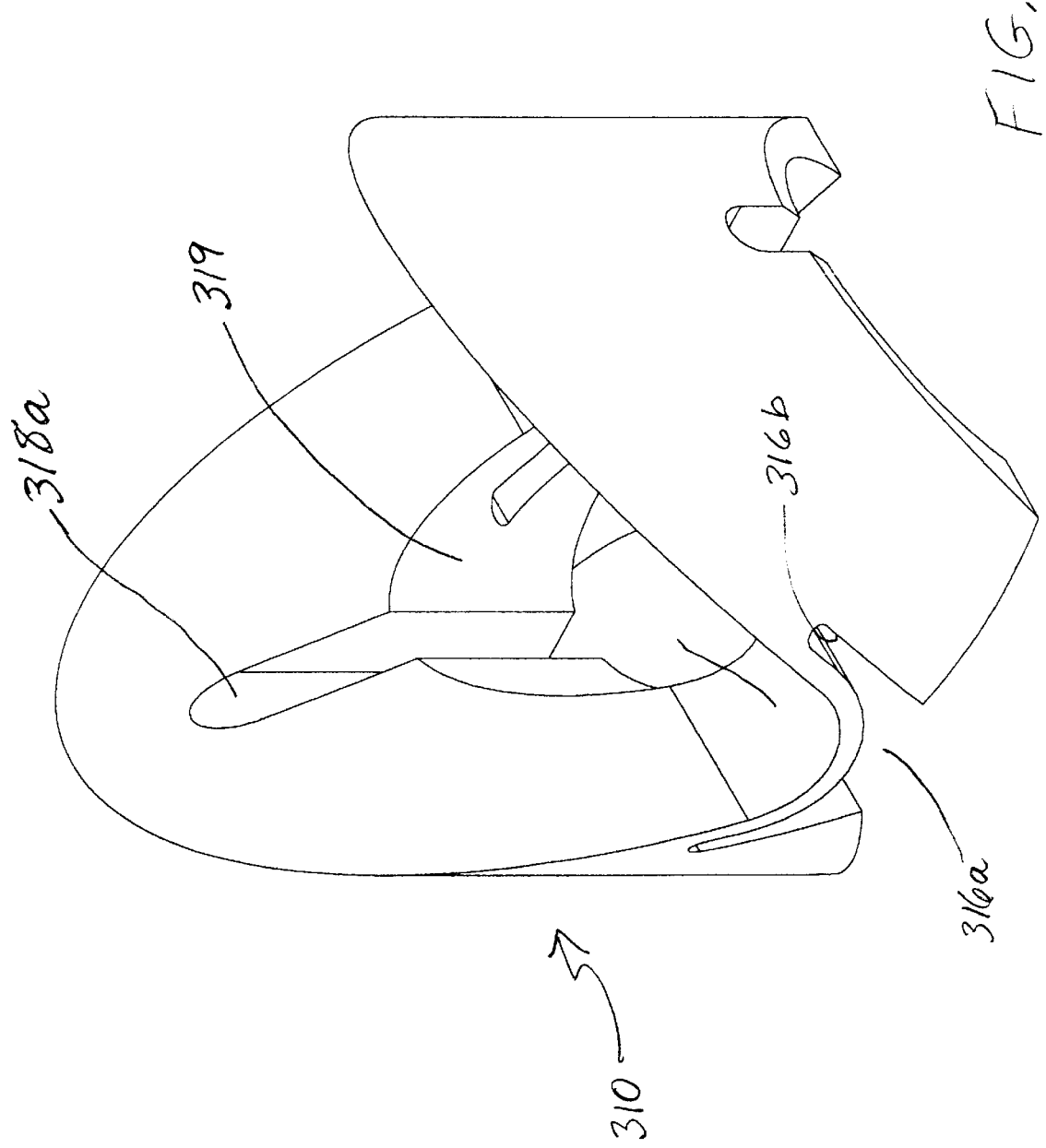

METHOD AND APPARATUS FOR ATTACHING CONNECTIVE TISSUES TO BONE USING A CORTICAL BONE ANCHORING DEVICE

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it is able to be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures are of the arthroscopic type, and are considered investigational in nature.

Another significant difficulty with current arthroscopic rotator cuff repair techniques are shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

An approach that also utilizes the difference in density between the cortical and cancellous layers of bone is described in U.S. Pat. No. 5,618,314 to Harwin, et al. In that design, the anchor device uses stationary wing members which extend proximally and radially outward from the anchor member and which employ a cutting means along the wing members. In this approach, the anchor device is inserted into a hole which has been drilled into the bone and then rotated radially such that the wing members with the cutting means are disposed into the cancellous layer of bone just below the cortical bone. With this device, a relatively small surface area of the wing members are disposed against the cortical bone in comparison with the present invention, making it more prone to being pulled out of the bone structure as proximal tension is applied to the suture.

A number of other various methods of anchoring a suture to bone utilizing the difference in density between the cortical and cancellous bone are described in U.S. Pat. No. 5,417,691 to Hayhurst. One such method describes an anchor with a series of proximally pointing barbs along its member, which is inserted, into a hole in the bone structure, utilizing the barbs as a means of anchoring the device to the bone. This method presents the same disadvantage with respect to the amount of surface area in contact with the bone as described in connection with the Harwin, et. al. patent, supra.

The Hayhurst patent further describes an approach to anchoring a suture to bone using an elongated anchor member shaped to normally assume a straight configuration which is then bent or flexed to allow it to be inserted through a needle or lumen and then expelled such that it returns to its straight configuration in a position generally perpendicular to the suture. This approach is designed for applications in which the anchor member may be placed between cartilage and bone and is impractical for use where the suture must be anchored directly to the bone—the applications for which the present invention is specifically designed.

Other similar approaches are described in U.S. Pat. No. 5,417,712 to Whittaker, et al. This patent describes anchor devices using various different barbs and wings to secure the anchor members to the bone. This approach, however, suffers the disadvantage of a small surface area disposed against the bone and a relatively weak construction and resultant anchoring interface.

Bone anchor designs utilizing a means of disposing an anchoring device below the cortical bone in a generally parallel position to the cortical bone and in a perpendicular position to the suture are described in U.S. Pat. No. 5,941,900 to Bonutti and in U.S. Pat. No. 6,045,574 to Thal. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out.

These anchors, however, do not have the ability to be bent or flexed for deployment through a narrow lumen or hypotube, making insertion and placement difficult. They also suffer from the same disadvantage of a small surface area to be disposed against the cortical bone as the other applications described above.

U.S. Pat. No. 6,146,406 to Shluzas et al. discloses a bone anchor having first and second anchoring legs and a bridge joining the anchoring legs between their proximal and distal ends. Portions of the anchoring legs on a proximal side of the bridge are configured to elastically compress together in response to an insertion force applied to the bone anchor during insertion of the bone anchor into a bone hole, and to plastically splay apart in response to a withdrawal force applied to the bone anchor, which force is applied by pulling on the suture extending proximally from the surgical site. This anchor also has a relatively limited surface area contact with the lower surface of the cortical bone and with the surrounding cancellous bone, and can be difficult and tricky to insert and deploy.

What is needed, therefore, is a new approach for repairing the rotator cuff or fixing other soft tissues to bone, wherein the suture resides completely below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

SUMMARY OF THE INVENTION

The present invention overcomes the disadvantages of prior art devices and provides further advantages by utilizing the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone.

A major aspect of the present invention is to provide a means to either attach a suture securing device to the inventive anchoring device, or to attach a suture directly to the inventive device outside the body, then deploy the entire apparatus into the procedural area through a lumen in a tube. Once inserted into the procedural area within the bone, the device is expanded to anchor it beneath the cortical layer of bone. When the device is deployed, it extends radially into the cancellous bone just beneath the cortical layer of bone at the point at which the cortical and cancellous layers of bone meet. The manner in which the present invention is designed prevents it from returning, after it has been deployed, to the folded or bent profile it assumed as it was being deployed. This design, moreover, prevents the invention from moving proximally due to the density of the cortical bone against which it is seated, or from moving either distally or radially due to the amount of anchor surface area which is extended into the cancellous bone. This approach is practicable for use in an arthroscopic procedure and eliminates the disadvantages associated with the use of screws, tacks, and staples described above. The present invention solves the problems outlined above by providing innovative bone anchor and connective techniques which permit a suture attachment which lies beneath the cortical bone surface, without the necessity of tying knots.

More particularly, there is provided in a preferred embodiment a bone anchor device for attaching connective tissue to bone, which comprises disk adapted for insertion into a portion of bone. The disk is movable between a bent orientation for presenting a smaller cross-section and an expanded orientation for presenting a larger cross-section, and the disk is substantially planar when in the expanded orientation. The bent orientation is utilized for inserting the disk through a small hole into a region of cancellous bone beneath the cortical bone layer, after which the disk is actuated to move into its expanded orientation so that it will be permanently anchored in the cancellous bone, as it will be too large to return proximally through the hole in the cortical bone layer. The disk is generally elliptical when in the expanded orientation, and presents a generally circular footprint when in the bent orientation and viewed from a proximal position.

In one preferred embodiment, the substantially planar disk is annular, comprising an annular sidewall and a center aperture. Such an embodiment is particularly useful with a separate suture retaining anchor disposed distally of the disk. Two axial suture receiving grooves disposed on an inner surface of the annular sidewall, spaced from one another by approximately 180 degrees, are preferably employed.

In another embodiment, wherein the disk itself may be utilized as the suture retaining anchor, the substantially planar disk is substantially solid, having two small apertures adjacent to one another in a center portion thereof for receiving suturing material therethrough.

A slit is preferably disposed in the disk for facilitating the movement of the disk between the bent orientation and the expanded orientation, and, more preferably, two such slits, spaced approximately 180 degrees apart, are employed. The disk has a longitudinal axis extending between a proximal end and a distal end thereof, wherein the disk bends about an axis which lies transversely to the longitudinal axis. The disk forms a generally "V" shape in the bent orientation. In a preferred embodiment, each slit comprises an axial portion extending from the distal end of the disk, and a circumferential portion extending about a portion of an outer sidewall of the disk, wherein the circumferential portion is in communication with the axial portion so that the two slit portions together form each generally "T" shaped slit. A thin axial length of the sidewall extends between the proximal end of the disk and the circumferential slit portion. The disk bends about the transverse axis in a region including the thin axial length of each of the two slits. In one embodiment, wherein the disk is formed of flat stock resilient material, such as spring steel, tension applied to opposing edges of the disk cause the bending to occur, because the natural orientation of the disk is its expanded planar configuration. In another embodiment, however, wherein the disk is formed from tubular stock, which is a non-resilient material, such as stainless steel, an axial compressive force applied to the disk causes the bending to occur. In this configuration, the natural orientation of the disk is its bent, reduced configuration, and the axial compressive force is applied to force the disk to its expanded flat configuration.

In preferred embodiments, the disk has a thickness of approximately 0.031 inches and the thin axial length of the sidewall is approximately 0.006 inches long. As noted supra, in one embodiment, it comprises spring stainless steel, and is biased by the spring stainless steel to assume the expanded orientation unless otherwise constrained. In a second embodiment it comprises ordinary stainless steel or other suitable biocompatible material, and must be forced into the expanded orientation.

In another embodiment, designed to substantially increase the pull-out strength of the anchor, a plurality of the aforementioned disks, arranged in a stacked array, are employed.

In another aspect of the invention, there is provided a bone anchor apparatus, which comprises a first tube, a second tube coaxially and slidably disposed within the first tube, and a disk which is movable between a bent orientation for presenting a smaller cross-section and an expanded orientation for presenting a larger cross-section. During deployment of the bone anchor, the disk is disposed within the first tube distally of the second tube, in the aforementioned bent orientation, with a distal end of the second tube engaging the disk. In the spring steel embodiment, tension applied to opposing edges of the disk by an inner wall of the first tube cause the bending to occur. In a preferred embodiment, the first tube comprises a proximal end portion having a first diameter and a distal end portion having a second diameter which is reduced relative to the first diameter. An axial length of the distal end portion is approximately equal to a thickness of cortical bone in a portion of bone into which the disk is to be disposed to function as a bone anchor, wherein a transition region on the tube between the proximal and distal end portions is adapted to function as a stop when the first tube is inserted into a hole in the bone portion, thereby ensuring that a distal end of the first tube is disposed in cancellous bone beneath the cortical bone thickness.

Preferably, there is disposed a slit in an outer wall of the first tube, which slit extends proximally from the distal end of the first tube proximally of the transition region. Additionally, there is a slit in an outer wall of the second tube, wherein the first and second tubes are rotationally oriented relative to one another, when the second tube is disposed within the first tube, so that the slits in each of the first and second tubes are substantially coincident with one another.

In still another aspect of the invention, there is provided a bone anchor apparatus which comprises an anchor body having a first displaceable portion and a second displaceable portion, together with a connecting portion which joins the first and second displaceable portions. Advantageously, the first and second displaceable portions are each moveable from a first orientation wherein portions of each of the first and second displaceable portions are disposed proximally of the connecting portion, and a second orientation wherein the first and second displaceable portions and the connecting portion all lie in substantially the same plane. Preferably, the first and second displaceable portions in combination with the connecting portion comprise a disk, and a suture receiving groove is disposed in each of the first and second displaceable portions. In a presently preferred embodiment, the anchor body is initially disposed in the first orientation.

In yet another aspect of the invention, there is disclosed a method for securing connective tissue to bone. The inventive method comprises steps of securing a first end of a length of suture to a portion of soft tissue to be attached to a portion of bone, and threading a second end of the length of suture through an aperture in a body of a bone anchor disk. The bone anchor disk is disposed within a lumen of a tube, with the disk being disposed in a bent orientation having a reduced cross-section. A distal end of the tube is inserted into a hole within the portion of bone. The disk is then deployed from the distal end of the tube. Once deployed, the disk moves to an expanded orientation, so that the disk becomes anchored within the portion of bone.

In still another aspect of the invention, there is disclosed a method of fabricating a bone anchor device. The inventive method comprises steps of providing a tube of biocompatible material, forming a bone anchor device by making a series of cuts on a first end of the tube, and separating the bone anchor device from a remaining portion of the tube by making a further cut through the tube.

The invention, together with additional features and advantages thereof, may best be understood by reference to the following description taken in conjunction with the accompanying illustrative drawing.

BRIEF DESCRIPTION OF THE DRAWINGS

FIG. 6 is a schematic view, in cross-section, illustrating a preferred method for deploying the inventive bone anchor device;

FIG. 6A is a cross-sectional view of the area identified by the circle labeled 6A in FIG. 6, showing insertion of the inventive bone anchor device into a suitable bone site;

FIG. 6B is a cross-sectional view similar to FIG. 6A showing the bone anchor device after deployment;

FIG. 7 is a perspective view of an alternative embodiment of the inventive anchor device, which may be utilized without an associated suture securing device;

FIG. 8b is a top (proximal) view of the embodiment of FIG. 8a;

FIG. 9b is a top (proximal) view of the embodiment of FIG. 9a;

FIG. 10 is a perspective view of a tube of suitable material for fabricating an embodiment of the inventive anchor device using an alternative fabrication method;

FIG. 14 is a perspective view from one end of the inventive anchor device fabricated from the tube shown in FIG. 10; and FIG. 15 is a perspective view from the side of the inventive anchor device of FIG. 14.

DESCRIPTION OF THE PREFERRED EMBODIMENT

Figure 1:
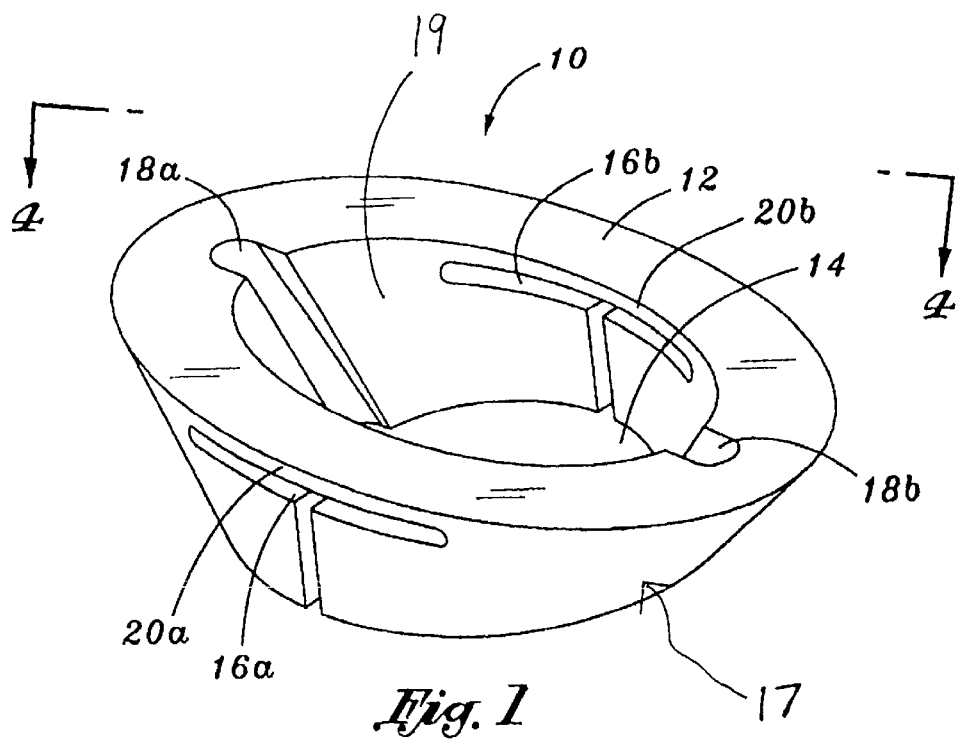
FIG. 1 is a perspective view of a presently preferred embodiment of the inventive bone anchor device, shown in a fully expanded configuration.

Referring now more particularly to the drawings, there is shown in FIG. 1 a bone anchor 10 constructed in accordance with an embodiment of the present invention, comprised of an elliptical disk 12 with a generally circular aperture 14 in its center. In this first embodiment, the disk 12 is fabricated of flat stock, preferably 301 stainless spring steel, or other biocompatible equivalent material, and has a thickness of approximately 0.031 inches. First and second slits 16a and 16b, respectively, formed in a generally "T" shape when viewed from the side, are cut into each side of the annular disk from its distal end, using electro-discharge machining (EDM) techniques, or the like, and are spaced approximately 180 degrees from each other about the periphery of the disk. The "T" shaped slits 16a, b are cut entirely through the annular sidewall 17 of the disk 12, and function to allow the disk to be bent in an upward or proximal direction for deployment into a portion of bone, as shall be more particularly described in connection with FIG. 2, below, and also to prevent "bend-back" when the disk returns to its flat or unfolded configuration (meaning that the slits will assist in preventing the disk from over-bending into a downward or distal direction as it returns to its unfolded configuration). The circular aperture 14 has first and second axially oriented grooves or channels 18a and 18b, respectively, in its inside surface 19, which are preferably spaced approximately 180 degrees apart and are offset about 90 degrees from each slit 16a, b. The aperture 14 permits the deployment of a suture securing apparatus into the desired bone structure distally through the inventive device, and also receives and permits passage of suture material therethrough.

Figure 2:
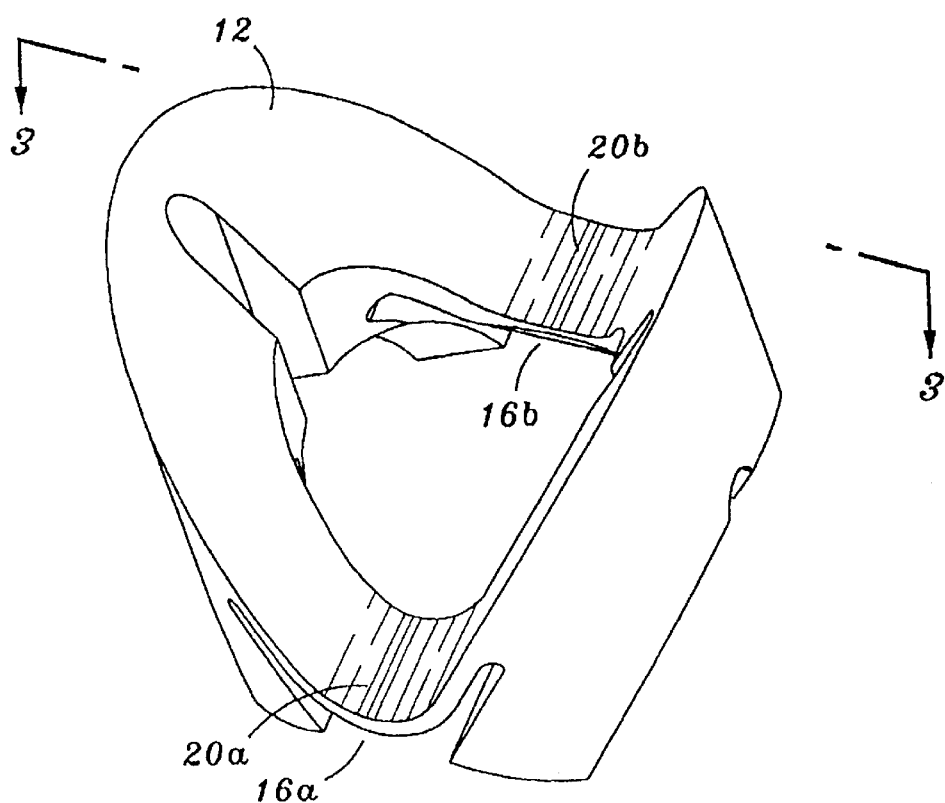
FIG. 2 is a perspective view similar to that of FIG. 1, illustrating the inventive bone anchor device in a folded configuration.

In FIG. 2 the elliptical disk 12 has been bent upward or proximally into what might be described as a generally "V" shape by exerting tension on each end of the disk at locations about 90 degrees displaced from each of the "T" shaped slits 16a, b. Such applied tension, the application of which in the illustrated embodiment will be discussed in greater detail hereinbelow, causes the thinner area 20a, 20b of the proximal end of the disk formed as a result of the presence of the T shaped slits 16a, 16b, which is preferably fabricated to have a thickness of approximately 0.006 inches from the proximal end of the T shaped slit to the proximal end of the disk 12, to bend about an axis X (FIG. 3), which axis lies generally transversely to a longitudinal axis Y (FIG. 5) for as long as such tension is continually exerted. When the tension is released, the spring-like action of the thinner profile formed at the proximal ends of such "T" shaped slits 16a, b acts to cause the disk to return to its original flat profile.

Figure 3:
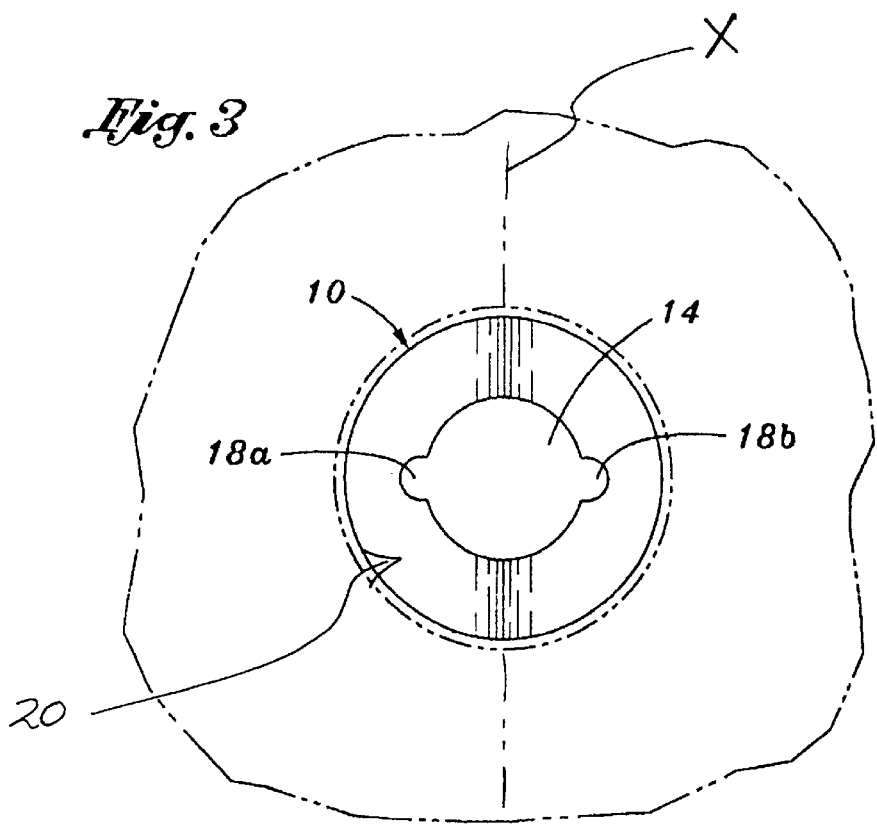
FIG. 3 is a proximal plan view of the inventive bone anchor device wherein tension has been applied to each end of the device so that it is held in a circular profile.

FIG. 3 is a proximal view of the inventive device as it appears with tension being applied to each end of the elliptical disk as described in connection with FIG. 2, above. It can be seen from FIG. 3 that applying such tension to the disk 12 causes it to be held in a circular profile. This circular profile allows the device to be inserted into a length of hypotubing for deployment arthroscopically into the desired surgical area by means of a trocar. The device is inserted through a length of hypotubing such that it is deployed at the juncture between the cancellous and cortical bone structures as shall be more fully illustrated hereinbelow.

Figure 4:
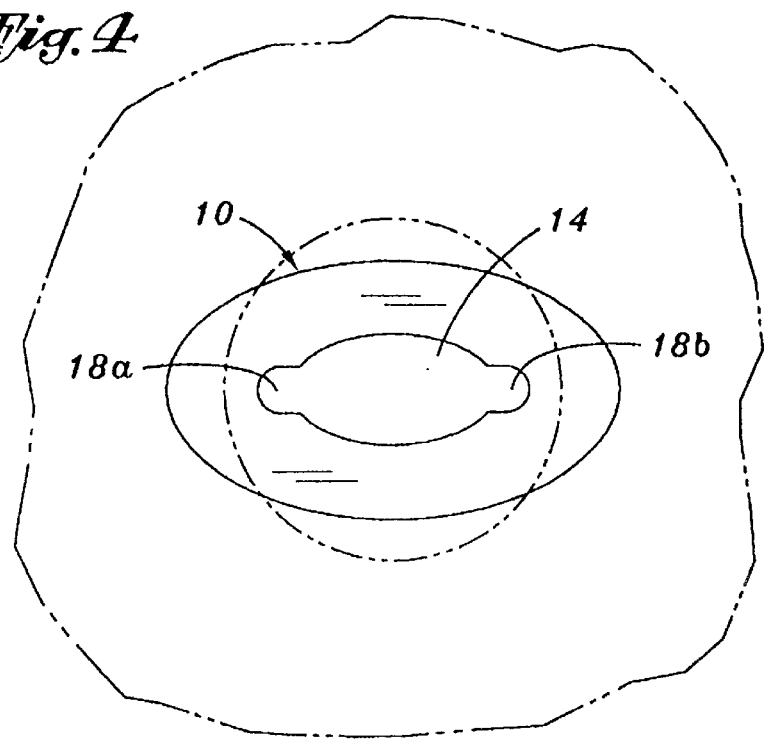
FIG. 4 is a proximal plan view of the inventive bone anchor device, similar to that of FIG. 3, wherein tension is no longer applied to each end of the device, so that it re-assumes an elliptical shape.

FIG. 4 is a proximal view of the inventive device as it appears once the referenced tension is no longer applied to each end of the elliptical disk 12. It can be seen from FIG. 4 that once the tension is released, the disk 12 springs back to its original elliptical shape as viewed from a proximal direction as well as to its original flat profile as viewed from the side. As the disk 12 returns to its original profile, the two ends of the elliptical disk are pushed into the cancellous bone structure just below the point where the cancellous bone meets the cortical bone. When the disk 12 is returned to its original flat profile, its profile as viewed from a proximal direction returns from a round to an elliptical profile. Accordingly, with such a profile, the disk 12 is larger in cross-section than is the cross-sectional width of the hole in the bone structure into which it is inserted, such that the device 10 is anchored against the cortical bone in much the same way that a "moly" bolt becomes anchored within a wall or ceiling when it is radially expanded after insertion into the wall or ceiling through a drilled hole. The method by which the device is anchored to the bone structure shall be more fully described and illustrated in conjunction with FIGS. 5 & 6 below.

Figure 5:
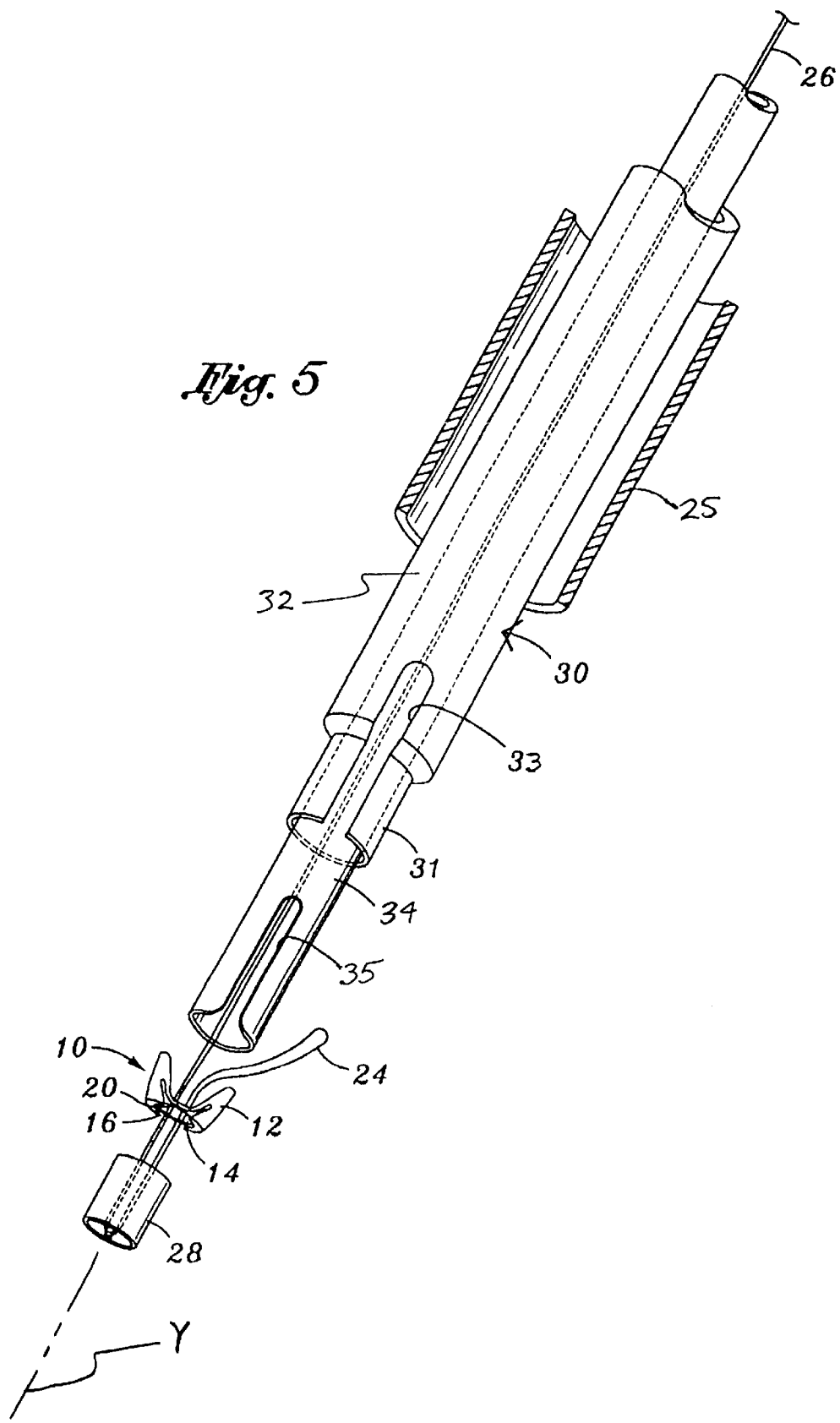
FIG. 5 is a perspective view illustrating a preferred apparatus and method for inserting the inventive bone anchor device.

Referring now to FIG. 5, a presently preferred apparatus by which the bone anchor 10 is deployed into desired bone structure (in the preferred case, a humeral head) to secure soft tissue to bone will be described. Initially, a suture 24, is stitched in a suitable manner to the soft tissue to be repaired (preferably, a rotator cuff tendon, which is not shown in this figure). The stitching process may be accomplished by any known means, and any known suture stitch may be employed, the objective being to employ a secure stitch so that the suture is not inadvertently separated from the tendon after completion of the repair procedure, necessitating reentry to the surgical site. In preferred approaches, the suture is attached to the soft tissue using a "mattress stitch", which is well known in the art as being a particularly secure stitch which is unlikely to fail postoperatively.

Of course, as discussed supra, the preferred repair procedure discussed herein is an arthroscopic procedure, wherein an initial access incision is made to the repair site, and a trocar 25 is inserted into the access incision to provide access to the repair site for surgical instruments as well as optical instruments. Preferably, a suturing instrument is inserted into the trocar to perform the aforementioned suturing step. Of course, the inventive device may also be utilized in an open surgical procedure, if desired, wherein the sutures are manually placed.

Once the suturing process is completed, the free ends 26 of the suture 24 are removed proximally through the trocar 25 from the patient's body, together with the suturing instrument. The free ends 26 of the suture 24 may then be attached to a suture anchoring device in the patient's body, which device may be integral with the bone anchor 10 or separate therefrom. The specifics of such suture anchoring systems are beyond the scope of the present invention, so, for the purposes of this description, a simple cylindrical suture anchoring device 28 through which the free ends 26 of the suture 24 have been threaded is shown.

Once the free ends 26 of the suture 24 are threaded through the suture securing device 28, they are threaded proximally through the aperture 14 in the bone anchor 10. The grooves 18a, 18b are useful for receiving the suture which passes through the aperture 14. The suture securing device 28 and bone anchor 10 are then inserted distally into a length of hypotubing 30 which includes a reduction in diameter at its distal end 31 so that its distal end is narrower than its proximal end 32. The narrower distal end 31 of the hypo tube 30 is adapted to fit into a hole which has been drilled into the bone structure (not shown in FIG. 5) such that the distal end of the hypotube will be disposed at a depth approximately equal to the depth of the cortical bone and cancellous bone interface. In other words, the length of the narrower distal end 31 of the hypo tube 30 is predetermined to coincide with the approximate thickness of the outer cortical layer of bone, so that the portion of tubing which is stepped outwardly from the smaller diameter of the distal end of the tube to the larger diameter of the proximal end of the tube acts as a stop, thereby ensuring that the anchor 10 will be disposed at the approximate junction of cortical and cancellous bone. A slit 33 is disposed in the distal end of the hypotube 30 to allow the hypotube 30 to be inserted into the hole disposed in the bone without interfering with the bound end of the suture 24 which has been stitched through the rotator cuff.

In one method of the present invention, a mandrel 34, made from a narrower length of hypotubing than the notched hypotube 30, is inserted distally into the hypotube 30 proximally from the bone anchor 10. The mandrel 34 has a rounded distal end that fits into and engages the proximal end of the disk 12 when the disk 12 is held into the aforementioned generally "V" shape as a result of the tension applied to its ends by the inside wall of the hypotube 30. A slit 35 is disposed in the distal end of the mandrel 34, in alignment with the corresponding slit 33 in the hypotube 30 when the mandrel 34 is inserted coaxially into the hypotube 30. Again, the slits 35 and 33 function to prevent the apparatus from interfering with the bound ends of the suture 24 as the apparatus is inserted into the hole in the bone structure. It is noted that the free ends 26 of the suture 24 pass proximally from the suture securing device 28, through the bone anchor 10 and mandrel 34 and out of the body, so that they may be manipulated by the practitioner performing the procedure.

The entire apparatus, consisting of the hypotube 30 with the suture securing device 28, the bone anchor device 10, and the mandrel device 34, all disposed coaxially within the hypotube 30, can now be inserted distally through the trocar 36 into the desired surgical site, such as, preferably, the shoulder of a patient.

To deploy the bone anchor 10 through the hypotube 30, the mandrel 34 is pushed in a distal direction against the bone anchor 10, pushing the bone anchor 10 out of the hypotube 30 and into the bone structure. When the bone anchor 10 is pushed completely out of the hypotube 30, so that tension is no longer applied to the ends of the elliptical disk 12 by the internal surface of the hypotube 30, the disk 12 returns from the generally "V" shaped profile exhibited while inside the hypotube 30 (FIGS. 2 and 3) to its original flat profile (FIGS. 1 and 4). This causes the ends of the elliptical disk 12 to push or dig into the soft cancellous bone just below the surface of the cortical bone layer.

Once the disk 12 along with the suture securing device 28 have been inserted into the bone structure, the hypotube 30 and mandrel 34 are removed through the trocar 25 out of the body. The free ends 26 of the suture 24 are then pulled in a proximal direction by the surgeon, in order to permit the soft tissue which is being reattached to adjacent bone structure to be adjusted positionally as necessary. This will also exert a distal force on the disk 12, which force acts to secure the disk in position against the cortical bone and to further secure the disk in its flat profile. As described in connection with FIG. 3, above, the flat profile of the disk 12 is larger than the diameter of the hole 42, making it very difficult or impossible to pull the disk proximally out of the bone structure.

In FIGS. 6, 6A, and 6B, there is shown a cross-sectional view of a human shoulder 40 on the left side of the body as seen from the front of the body and which illustrates a rotator cuff tendon 44 which is disposed across a humeral head 46. It is to be understood that, in this illustration, the rotator cuff tendon 44 is not 15 attached to the humeral head 46 at the interface 48 between the two. The humeral head 46 is comprised of an outer surface of cortical bone 49 and inner cancellous bone 50. In one method of use of the above described inventive anchor 10 and associated apparatus, the anchor 10 is utilized to assist in the repair of the shoulder 40 by reattachment of the rotator cuff tendon 44 to the humeral head 46.

To that end, as described supra, a trocar 25 is first inserted into the shoulder in proximity to the area where the rotator cuff tendon 44 is to be reattached to the humeral head 46, to allow for arthroscopic access. A hole 51 has been made, preferably by drilling or punching, in the desired location through the cortical bone 49 and into the cancellous bone 50. This illustration is intended only to provide a simple structural overview of the physiological elements involved in a typical situation where it is to be desired that soft tissue such as the rotator cuff tendon 44 be reattached to a humeral head 46.

Referring in particular to FIG. 6B, the bone anchor 10 is shown in its fully deployed state. The disk 12 is in its original flat profile just below the cortical bone 49 and inserted into the cancellous bone 50. The suture 24 is stitched through the rotator cuff tendon 44, threaded through the suture securing device 28, and the bone anchor 10, and then the loose ends 26 of the suture 24 pass through the trocar 25 and out of the patient's body. Proximal tension may be applied by the practitioner to the free ends 26 of the suture 24, to thereby secure the bone anchor device 10 against the cortical bone 49 and prevent the bone anchor device 10 from being removed from the bone structure.

FIG. 7 illustrates an alternative embodiment of the present invention wherein the anchor device 10 may be utilized without any independent suture securing device, such as suture anchoring device 28 shown in FIGS. 5 and 6. In this embodiment, rather than employing a single central aperture 14, two smaller apertures 14a, 14b are employed. A length of suture 24 may be threaded through the apertures 14a, 14b such that a portion 24a of the suture 24 may be pulled snugly against a distal surface 52 of the disk 12, thereby securing the suture to the disk 12. The two free ends 26 of the suture 24 may be knotted or otherwise secured together proximally of the anchor device 1 and the excess suture may then be cut and removed.

Figure 8A:
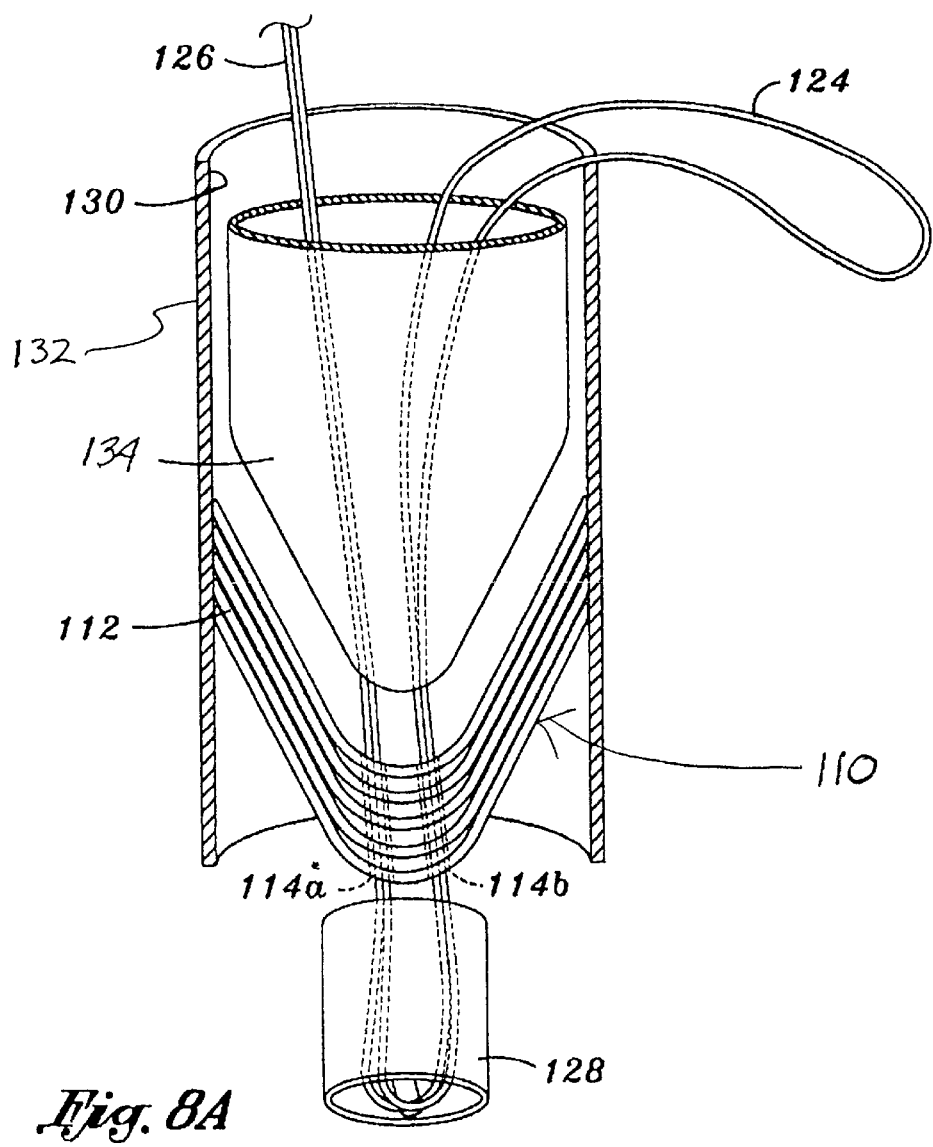
FIG. 8a is a plan view, in cross-section, of an alternative embodiment of the inventive anchor device, wherein a plurality of stacked elliptical disks are utilized rather than a single elliptical disk, as in the embodiments of FIGS. 1–7.
Figure 8B:
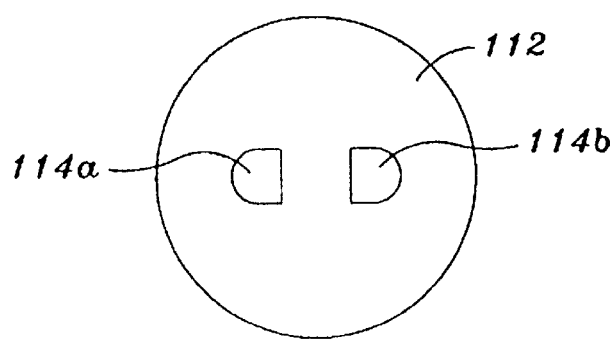

Referring now to FIGS. 8a and 8b, wherein like elements are designated by like reference numerals, preceded by the numeral "1", a further alternative embodiment of the present invention is illustrated. In these figures it can be seen that a stack of elliptical springs or disks 112 are utilized in place of the single elliptical disk employed in the previous embodiments, to together form the bone anchor device 110. It should be noted that the thickness of a single disk 112, approximately 0.031 inches in the preferred embodiments, is adequate to resist sufficient "pull-out" forces to be a useful anchor when used alone, but in certain applications it may be desirable to employ a stack of disks 112 in order to attain substantially greater resistance to pull-out forces. The elliptical springs 112 are held in a circular profile, like the single disk 12 in FIG. 2, by being inserted into a lumen 130 of a tube 132, so that the tube forces the disks into the circular profile. The stack of disks 112 is pushed distally through the lumen 130 by a mandrel 134 and is thereby deployed at the distal edge of the cortical bone in the same manner as described in connection with the embodiment of FIGS. 5 and 6 above. This embodiment is intended to be deployed using a suture anchoring device 128, as in FIG. 5, supra, though any type of suture attachment system could be employed if desired. FIG. 8b shows a top view of the embodiment, illustrating the round profile of the elliptical springs in their undeployed state, while still within the lumen 130.

Figure 9A:
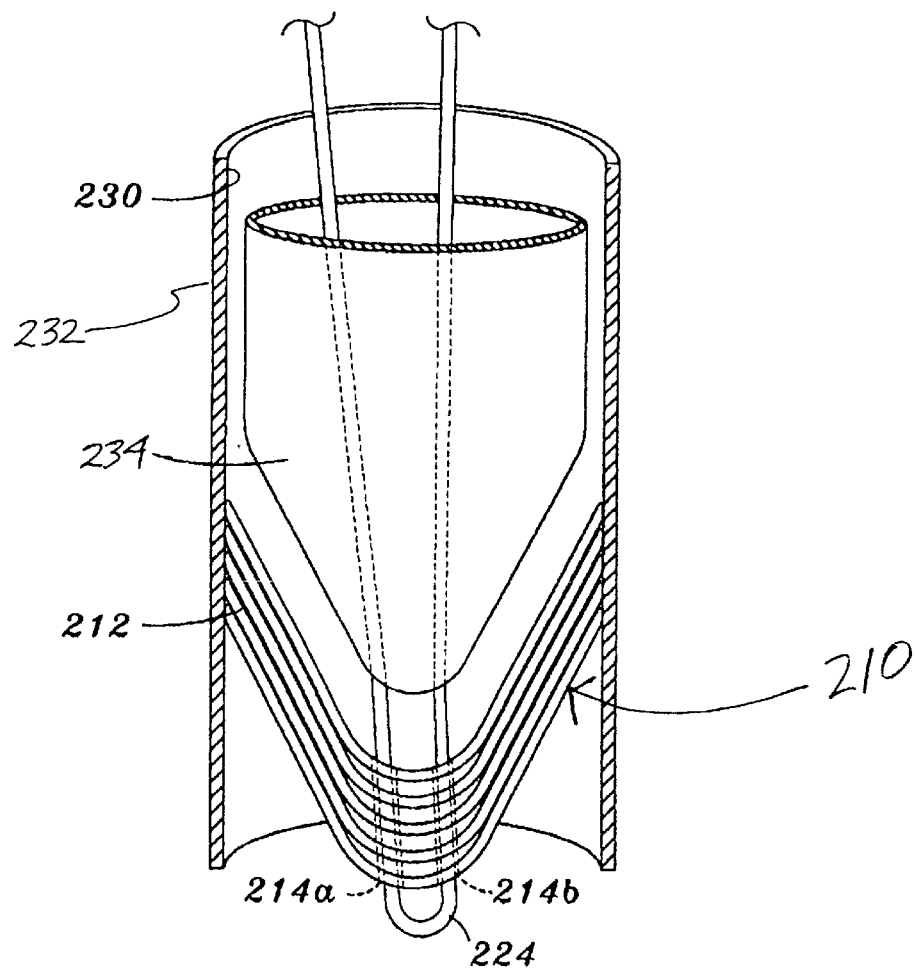
FIG. 9a is plan view, similar to FIG. 8a, of yet another alternative embodiment of the inventive anchor device.
Figure 9B:
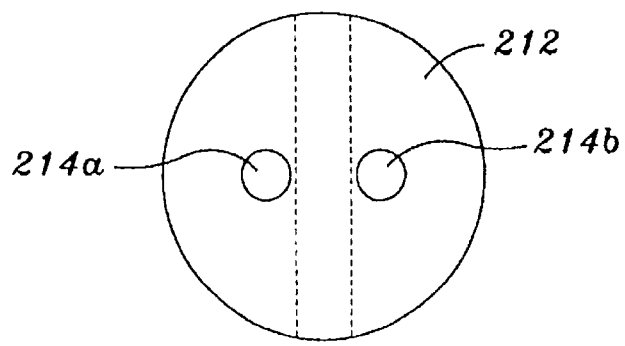

In FIGS. 9a and 9b, yet a third alternative embodiment is shown which is virtual identical to that shown in FIGS. 8a and 8b except that the device herein shown may be utilized without an independent suture securing device 128 as is the case with respect to the alternative embodiment shown in FIGS. 8a and 8b. In this embodiment, as illustrated, like elements to those of FIGS. 1–8b are designated by like reference numerals, preceded by the numeral "2". The suture 224 is secured directly by the bone anchoring device 210, by looping the suture through the suture holes 214a and 214b, as illustrated.

FIGS. 10–15 illustrate an alternative and more cost effective method for fabricating a bone anchoring device of the type disclosed in this patent application. In general, the bone anchor 310 as fabricated using the method of manufacturing to be described is similar in all respects to the bone anchor 10 as shown in FIGS. 1–7, except that, since it is fabricated from tubing, rather than from flat stock, its natural orientation is the bent orientation similar to that shown in FIG. 2. Once it has been inserted into suitable bone, an actuation device or the suture itself may be utilized to actuate the anchor 310 to its flat or unfolded deployed orientation.

Figure 11:
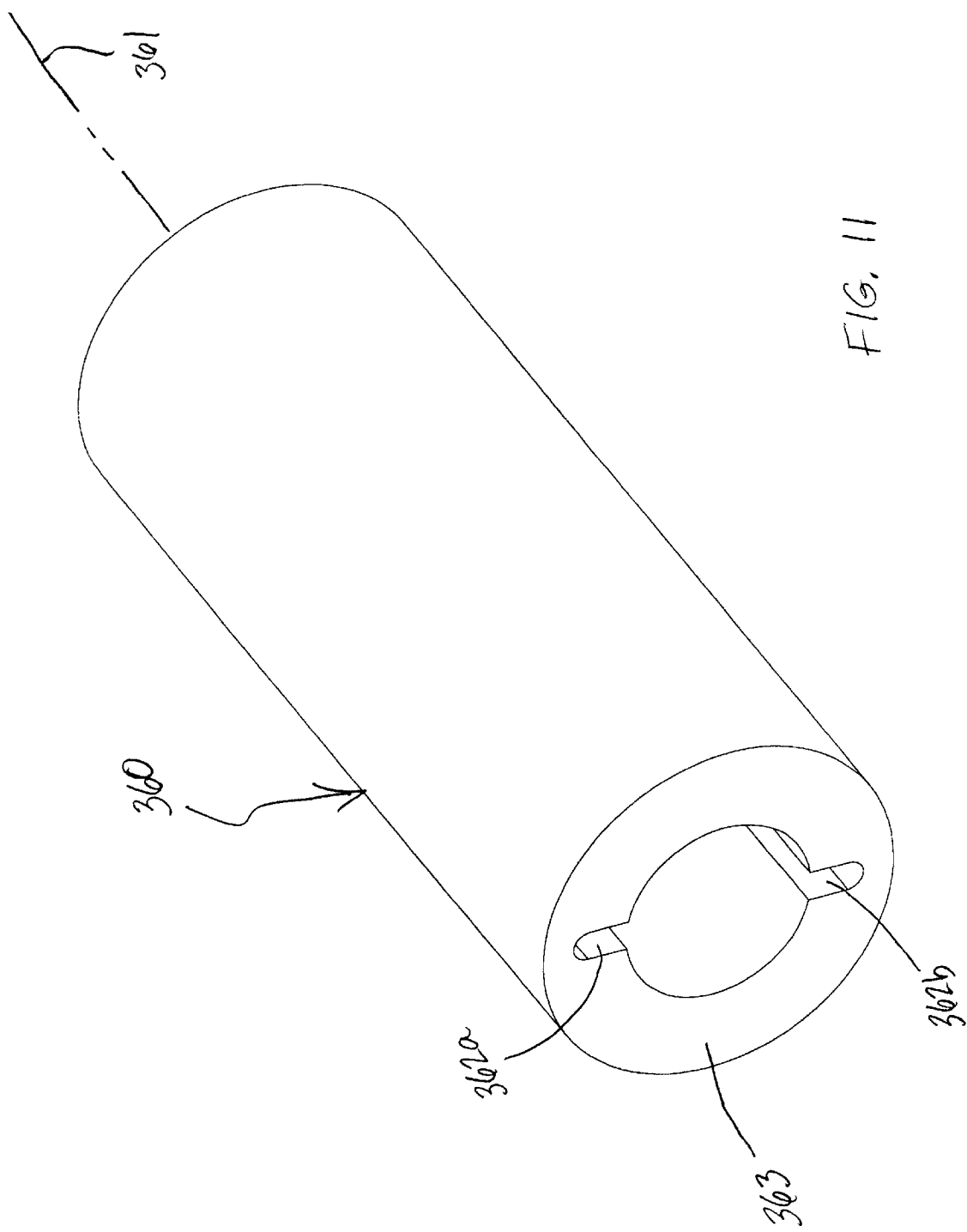
FIG. 11 is a perspective view similar to FIG. 10, illustrating the tube after a first fabrication step has been performed.
Figure 12:
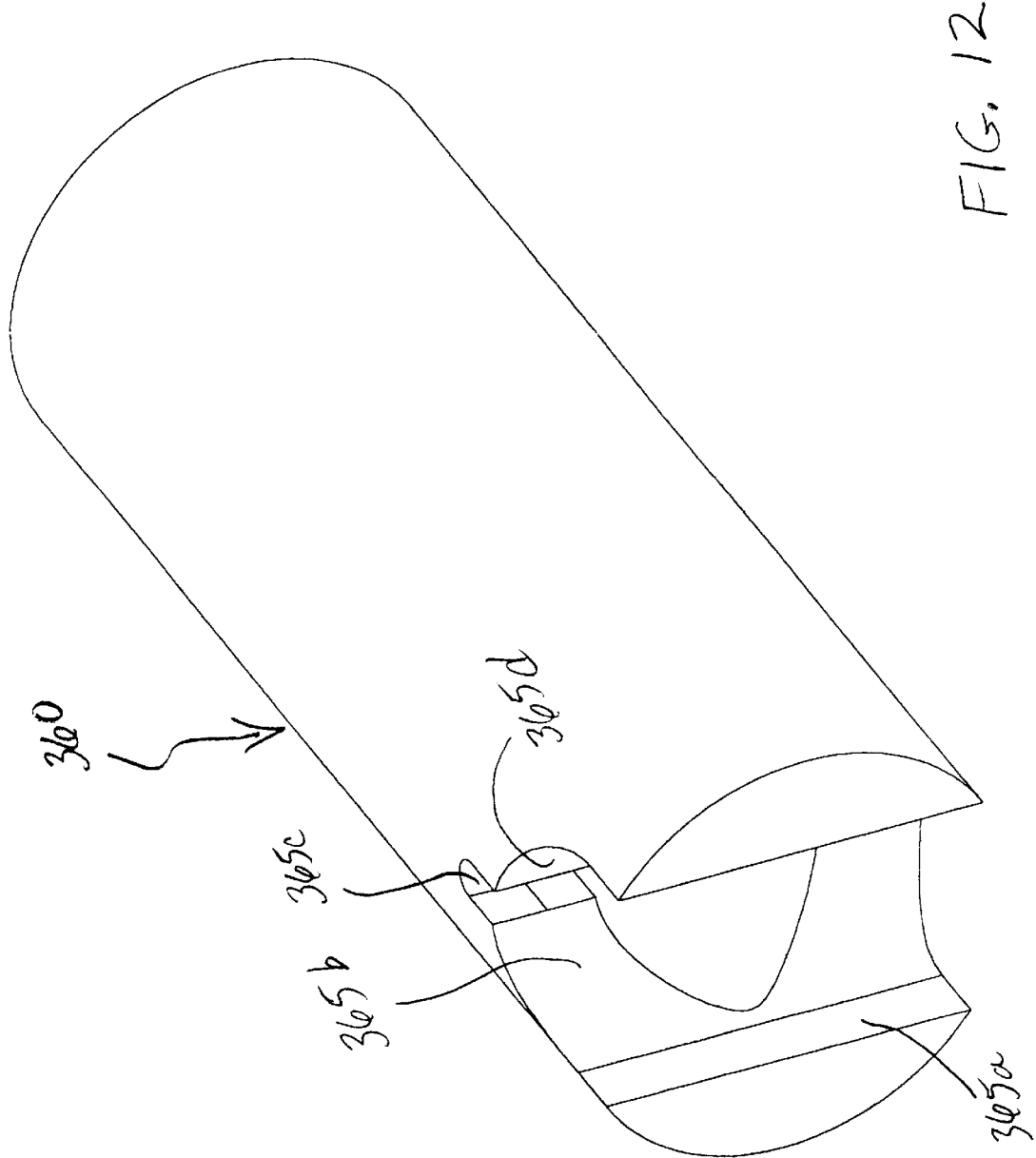
FIG. 12 is a perspective view similar to FIGS. 10 and 11 illustrating the tube after a second fabrication step has been performed.
Figure 13:
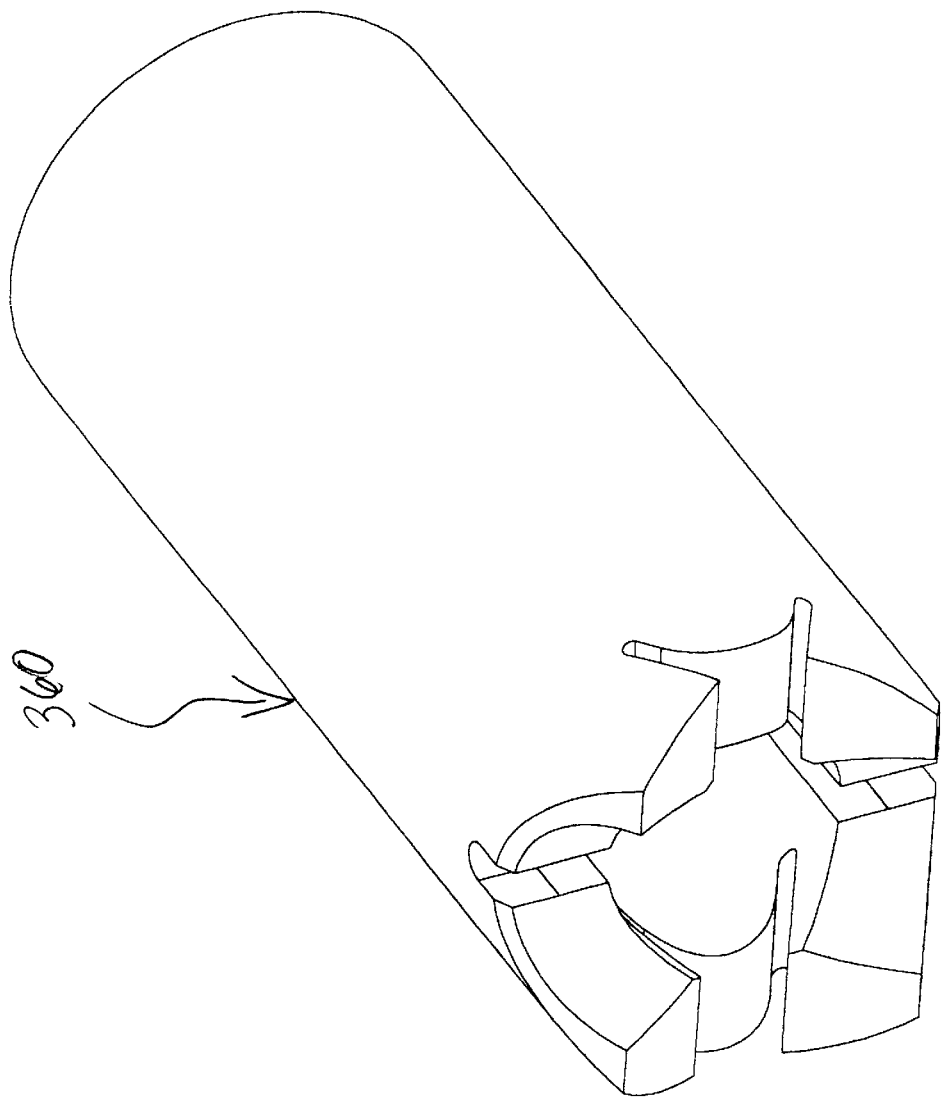
FIG. 13 is a perspective view similar to FIGS. 10–12 illustrating the tube after a third fabrication step has been performed.

More particularly, to fabricate the anchor 310 in accordance with the inventive method, a tube 360 of suitable biocompatible material, such as 300 series stainless steel, titanium, or carbon steel, and having a longitudinal axis 361, is provided (FIG. 10). As shown in FIG. 11, using EDM or other suitable cutting techniques, known to those skilled in the art, opposing axial channels 362a, 362b, extending from a first end 363 of the tube 360, are formed. Following this, additional cuts 365a–365d are made to remove material from the first end 363 of the tube 360, as shown in FIG. 12. The final fabrication of the anchor 310 configuration is illustrated in FIG. 13, wherein additional cuts have been made as shown, and in FIG. 14, which illustrates the anchor 310 after it has been separated from the remainder of the tube 310 by the completion of cut 367.

As is apparent from a comparison of FIGS. 2 and 15, the finished anchor 310 is substantially identical to the anchor 10, although an entirely different fabrication technique has been utilized. The advantage of the methods described in connection with FIGS. 10–15 is a dramatically lower cost of production and a substantially increased rate of production. The reason for the reduced cost of production, other than, of course, the increased rate of production, which naturally reduces costs proportionately, is the ability to use cheaper materials, and to minimize material waste. The tube 360 may be utilized to fabricate a number of anchors 310, and there is no need to use relatively expensive spring steel, because the natural orientation of the anchor 310, because it is fabricated from tubing 360, is the folded configuration shown in FIGS. 14 and 15. Thus, there is no need to bend the anchor 310 in order to insert it into the procedural site using the insertion tube 30. Accordingly, there is no need to utilize a material which is capable of expanding back into its natural state once it has been bent. In contrast, once the anchor 310 is properly positioned within the desired bone site, below the cortical bone layer, a deployment instrument or other suitable means may be used to move the anchor 310 proximally against the lower surface of the cortical bone. The force applied against the anchor 310 by the cortical bone as the anchor is moved proximally against it forces the anchor to bend into a substantially flat configuration, similar to that of FIG. 1, so that the anchor is permanently disposed within the bone to anchor the suture therein.

One approach is to deploy the anchor to its extended or flat configuration using the suture itself, rather than a separate deployment instrument. Thus, as discussed supra in conjunction with the FIG. 1 embodiment, once the anchor 310 is in place just beneath the cortical bone, the practitioner performing the procedure will pull the suture proximally, to approximate the soft tissue to the bone, as desired. As the suture is pulled proximally, it will exert a proximal force on the anchor 310, thereby pushing it against the cortical bone and forcing its deployment to the deployed, substantially flat orientation.

It is to be understood that the figures of the bone and anchors seen above are purely illustrative in nature, and are not intended to perfectly reproduce the physiologic and anatomic nature of the humeral head as expected to be seen in the human species, nor to limit the application of the inventive embodiments to repair of the rotator cuff. The invention is applicable to many different types of procedures involving, in particular, the attachment of connective or soft tissue to bone. Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A bone anchor device for attaching connective tissue to bone, comprising a disk which is adapted for insertion into a portion of bone, said disk being movable between a bent orientation for presenting a smaller cross-section and an expanded orientation for presenting a larger cross-section, said disk being annular, comprising an annular sidewall and a center aperture, and being substantially planar in said expanded orientation;
    said disk further comprising two axial suture receiving grooves disposed on an inner surface of said annular sidewall, said grooves being spaced from one another approximately 180 degrees.

2. A bone anchor device for attaching connective tissue to bone, comprising a disk which is adapted for insertion into a portion of bone, said disk being movable between a bent orientation for presenting a smaller cross-section and an expanded orientation for presenting a larger cross-section, said disk being substantially planar in said expanded orientation;
    wherein said disk is substantially solid, having two small apertures adjacent to one another in a center portion thereof for receiving suturing material therethrough.

3. A bone anchor device for attaching corrective tissue to bone, comprising a disk which is adapted for insertion into a portion of bone, said disk being movable between a bent orientation for presenting a smaller cross-section and an expanded orientation for presenting a larger cross-section, said disk being substantially planar in said expanded orientation;
    and further comprising a slit disposed in the disk for facilitating the movement of said disk between the bent orientation and the expanded orientation.

4. The bone anchor device as recited in claim 3, wherein said disk has a longitudinal axis extending between a first end and a second end thereof, said disk bending about an axis which lies transversely to said longitudinal axis, and forming a generally "V" shape in said bent orientation.

5. The bone anchor device as recited in claim 4, wherein said slit comprises an axial portion extending from the first end of the disk, and a circumferential portion extending about a portion of an outer sidewall of said disk, said circumferential portion being in communication with said axial portion so that the two slit portions together form a generally "T" shaped slit.

6. The bone anchor device as recited in claim 5, and further comprising a thin axial length of said sidewall extending between the second end of the disk and said circumferential slit portion.

7. The bone anchor device as recited in claim 6, wherein said disk has a thickness of approximately 0.031 inches and said thin axial length of said sidewall is approximately 0.006 inches long.

8. The bone anchor device as recited in claim 6, wherein said disk bends about said transverse axis in a region including said thin axial length.

9. The bone anchor device as recited in claim 4, wherein tension applied to opposing edges of said disk causes said bending to occur.

10. The bone anchor device as recited in claim 4, wherein an axial compressive force applied to said disk causes said bending to occur.

11. The bone anchor device as recited in claim 3, and further comprising a second slit disposed approximately 180 degrees from the first slit.

12. The bone anchor device as recited in claim 1, wherein said disk comprises spring stainless steel, and is biased by said spring stainless steel to assume said expanded orientation unless otherwise constrained.

13. The bone anchor device as recited in claim 1, wherein said disk is initially formed in said bent orientation.

14. A bone anchor device for attaching connective tissue to bone, comprising a disk which is adapted for insertion into a portion of bone, said disk being movable between a bent orientation for presenting a smaller cross-section and an expanded orientation for presenting a larger cross-section, said disk being substantially planar in said expanded orientation;
    and further comprising a plurality of said disks, arranged in a stacked array, for providing a higher pull-out force resistance than is possible using a single disk.

15. A bone anchor device for attaching connective tissue to bone, comprising a disk which is adapted for insertion into a portion of bone, said disk being movable between a bent orientation for presenting a smaller cross-section and an expanded orientation for presenting a larger cross-section, said disk being substantially planar in said expanded orientation;

wherein said disk is generally elliptical when in said expanded orientation, and presents a generally circular footprint when in said bent orientation and viewed from a proximal position.

16. A bone anchor apparatus, comprising:

a first tube;

a second tube coaxially and slidably disposed within said first tube; and a disk which is movable between a bent orientation for presenting a smaller cross-section and an expanded orientation for presenting a larger cross-section;

wherein said disk is disposed within said first tube distally of said second tube, in said bent orientation, a distal end of the second tube engaging said disk; and a suture retaining device disposed distally of said disk.

17. A bone anchor apparatus, comprising:

first tube;

a second tube coaxially and slidably disposed within said first tube; and a disk which is movable between a bent orientation for presenting a smaller cross-section and an expanded orientation for presenting a larger cross-section;

wherein said disk is disposed within said first tube distally of said second tube, in said bent orientation, a distal end of the second tube engaging said disk;

wherein said first tube comprises a proximal end portion having a first diameter and a distal end portion having a second diameter which is reduced relative to said first diameter, an axial length of said distal end portion being approximately equal to a thickness of cortical bone in a portion of bone into which said disk is to be disposed to function as a bone anchor, wherein a transition region on said tube between said proximal and distal end portions is adapted to function as a stop when said first tube is inserted into a hole in said bone portion, thereby ensuring that a distal end of the first tube is disposed in cancellous bone beneath said cortical bone thickness.

18. The bone anchor apparatus as recited in claim 17, and further comprising a slit in an outer wall of said first tube, said slit extending proximally from the distal end of said first tube proximally of said transition region.

19. A bone anchor apparatus, comprising:

a first tube;

a second tube coaxially and slidably disposed within said first tube; and a disk which is movable between a bent orientation for presenting a smaller cross-section and an expanded orientation for presenting a larger cross-section;

wherein said disk is disposed within said first tube distally of said second tube, in said bent orientation, a distal end of the second tube engaging said disk;

and further comprising a slit in an outer wall of said.first tube, extending proximally from a distal end of the first tube.

20. The bone anchor apparatus as recited in claim 19, and further comprising a slit in an outer wall of said second tube, the first and second tubes being rotationally oriented relative to one another, when the second tube is disposed within the first tube, so that the slits in each of said first and second tubes are substantially coincident with one another.

21. The bone anchor apparatus as recited in claim 16, and further comprising a center aperture in said disk for receiving suture material therethrough.

22. The bone anchor apparatus as recited in claim 16, and further comprising a slit disposed in the disk for facilitating the movement of said disk between the bent orientation and the expanded orientation.

23. The bone anchor apparatus as recited in claim 22, wherein said apparatus has a longitudinal axis which extends between a proximal end and a distal end of said disk, said disk bending about an axis which lies transversely to said longitudinal axis, and forming a generally "V" shape in said bent orientation.

24. A bone anchor apparatus, comprising:

a first tube;

a second tube coaxially and slidably disposed within said first tube; and a disk which is movable between a bent orientation for presenting a smaller cross-section and an expanded orientation for presenting a larger cross-section;

said disk being disposed within said first tube distally of said second tube, in said bent orientation, a distal end of the second tube engaging said disk;

a slit disposed in said disk for facilitating the movement of said disk between the bent orientation and the expanded orientation;

said apparatus having a longitudinal axis which extends between a proximal end and a distal end of said disk, said disk bending about an axis which lies transversely to said longitudinal axis, and forming a generally "V" shape in said bent orientation;

wherein said slit comprises an axial portion extending from said distal end of the disk, and a circumferential portion extending about a portion of an outer sidewall of said disk, said circumferential portion being in communication with said axial portion so that the two slit portions together form a generally "T" shaped slit.

25. The bone anchor device as recited in claim 24, and further comprising a thin axial length of said sidewall extending between the proximal end of the disk and said circumferential slit portion.

26. The bone anchor device as recited in claim 25, wherein said disk bends about said transverse axis in a region including said thin axial length.

27. The bone anchor device as recited in claim 23, wherein tension applied to opposing edges of said disk by an inner wall of said first tube cause said bending to occur.

28. A bone anchor apparatus, comprising:

a first tube;

a second tube coaxially and slidably disposed within said first tube; and a disk which is movable between a bent orientation for presenting a smaller cross-section and an expanded orientation for presenting a larger cross-section;

said disk being disposed within said first tube distally of said second tube, in said bent orientation, a distal end of the second tube engaging said disk;

a slit disposed in said disk for facilitating the movement of said disk between the bent orientation and the expanded orientation; and a second slit disposed approximately 180 degrees from the first slit.

29. A bone anchor apparatus, comprising:

a first tube;

a second tube coaxially and slidably disposed within said first tube; and a plurality of disks, arranged in a stacked array, which are each movable between a bent orientation for presenting a smaller cross-section and an expanded orientation for presenting a larger cross-section;

said disks being disposed within said first tube distally of said second tube, each in said bent orientation, a distal end of the second tube engaging said stacked array of disks.

30. A bone anchor apparatus, comprising:

a first tube;

a second tube coaxially and slidably disposed within said first tube; and a disk which is movable between a bent orientation for presenting a smaller cross-section and an expanded orientation for presenting a larger cross-section;

said disk being disposed within said first tube distally of said second tube, in said bent orientation, a distal end of the second tube engaging said disk;

wherein said disk is generally elliptical when in said expanded orientation, and presents a generally circular footprint when in said bent orientation and viewed from a proximal position.

31. A bone anchor apparatus, comprising:

an anchor body having a first displaceable portion and a second displaceable portion; and a connecting portion which joins said first and second displaceable portions;

wherein said first and second displaceable portions are each moveable from a first orientation wherein portions of each of the first and second displaceable portions are disposed proximally of the connecting portion, and a second orientation wherein the first and second displaceable portions and the connecting portion all lie in substantially the same plane; and a suture receiving groove in each of the first and second displaceable portions.

32. The bone anchor apparatus as recited in claim 31, wherein the first and second displaceable portions in combination with the connecting portion comprise a disk.

33. The bone anchor apparatus as recited in claim 31, wherein the anchor body is initially disposed in said first orientation.

\* \* \* \* \*